(12) United States Patent
Barak

(10) Patent No.: US 7,651,622 B2
(45) Date of Patent: *Jan. 26, 2010

(54) PROCESS AND COMPOSITIONS FOR THE DISINFECTION OF WATERS

(75) Inventor: Ayala Barak, Jerusalem (IL)

(73) Assignee: Bromine Compounds Limited, Beer-Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/244,204

(22) Filed: Oct. 2, 2008

(65) Prior Publication Data

US 2009/0107923 A1 Apr. 30, 2009

Related U.S. Application Data

(60) Continuation of application No. 11/853,426, filed on Sep. 11, 2007, now Pat. No. 7,449,120, which is a continuation of application No. 11/024,066, filed on Dec. 29, 2004, now Pat. No. 7,285,224, which is a continuation of application No. 10/226,927, filed on Aug. 23, 2002, now Pat. No. 7,067,063, which is a division of application No. 09/023,984, filed on Feb. 13, 1998, now Pat. No. 6,478,973, which is a continuation of application No. 08/639,708, filed on Apr. 29, 1996, now abandoned, which is a continuation of application No. 08/272,276, filed on Jul. 8, 1994, now abandoned, which is a continuation of application No. 07/892,533, filed on Jun. 1, 1992, now abandoned.

(30) Foreign Application Priority Data

Jun. 3, 1991 (IL) .......................................... 98352

(51) Int. Cl.
*C02F 1/50* (2006.01)
*C02F 1/76* (2006.01)
(52) U.S. Cl. .................. 210/756; 162/161; 210/764
(58) Field of Classification Search .................. 210/756
See application file for complete search history.

(56) References Cited

U.S. PATENT DOCUMENTS

| | | | |
|---|---|---|---|
| 1,378,644 A | 5/1921 | Baker | |
| 1,413,153 A | 4/1922 | Baker | |
| 1,581,115 A | 4/1926 | Harold | |
| 2,112,476 A | 3/1938 | Bowers et al. | |
| 2,443,429 A | 6/1948 | Marks et al. | |
| 3,222,276 A | 12/1965 | Rudolf et al. | |
| 3,328,294 A | 6/1967 | Self et al. | |
| 3,799,396 A | 3/1974 | Ashmead et al. | |
| 3,975,271 A | 8/1976 | Saunier et al. | |
| 4,431,729 A | 2/1984 | Falxa | |
| 4,566,986 A | 1/1986 | Waldmann | |
| 4,643,835 A | 2/1987 | Koeplin-Gall et al. | |
| 4,767,564 A | 8/1988 | Kitchens et al. | |
| 4,872,999 A | 10/1989 | Schild et al. | |
| 5,683,654 A | 11/1997 | Dallmier et al. | |
| 5,976,386 A | 11/1999 | Barak | |
| 6,132,628 A | 10/2000 | Barak | |
| 6,478,973 B1 | 11/2002 | Barak | |
| 7,052,614 B2 * | 5/2006 | Barak | 210/756 |
| 7,067,063 B2 | 6/2006 | Barak et al. | |
| 7,285,224 B2 | 10/2007 | Barak et al. | |
| 7,449,120 B2 * | 11/2008 | Barak | 210/756 |

FOREIGN PATENT DOCUMENTS

| | | |
|---|---|---|
| EP | 0 403 465 A | 12/1990 |
| GB | 253623 | 6/1926 |
| GB | 1 421 417 A | 1/1976 |
| GB | 1 600 289 A | 10/1981 |
| JP | 54 161592 A | 12/1979 |
| JP | 56-13512 | 3/1981 |
| WO | WO-89/12604 A1 | 12/1989 |

OTHER PUBLICATIONS

R. Trautschold "Its Control in Paper Making by Chlorine and Ammonia" —hemical Industries Jul. '36 pp. 27-29.
H. Harold "Chloamine Treatment Of Water in the Field" —Royal Army Medical Corps pp. 115-119.
S. Rideal "The Influence of Ammonia and Organic Nitrogenous Compounds on Chlorine Disinfection" —Journal of The Royal Sanitary Institute vol. XXXI, No. 2 Issued Mar. 1910 pp. 33-45.
G. Houghton "Observations on the Chlorination of Water Containing Free Ammonia and Naturally Occuring Bromide" —The Bromide Content of Underground Waters Partt II. Oct. 1946 pp. 324-328.
R. Chapin "Dichloro-Amine" —W.A> Noyes This Journal, 42, 2173 vol. 51 Jul. 1929 pp. 2112-2117.
J. Race "Chlorination of Water Chapter I Histrorical" —Chlorination of Water pp. 1-29.
J. Race "Chloramine" —Chlorination of Water Chapter IX pp. 115-131.
R. Martin et al. "Microbiological Control in Pulp and Paper Manufacture" —Techincal Association Papers, Series 23 Jun. 1940 No. 1 pp. 239-245.
L. Enslow "Ammonia-Chlorine Reactions and Chloramine Production" —Contract Record and Engineering Review, Mar. 11, 1931 pp. 291-295.
M. Schirtzinger "Chlorine Compounds for Microbiological Control" —Paper Mill News Jul. 29, 1963 pp. 18-25.
K. Holwerda "On the Control and The Degree of Reliability of the Chlorination-Process of Drinking-Water, In Connection With the Chloramin-Procedure and the Chlorination of Ammoniacal Water" —Laboratory of Purification of Water at Manggarai pp. 252-297.
J. Mcamis "Prevention of Phenol Taste With Ammonia" pp. 341-350.
R.Wolfe et al. "Inorganic Chloramines as Drinking Water Disinfectants: A Review" —Research and Technology Journal, May 1984 pp. 74-88.

(Continued)

*Primary Examiner*—Peter A Hruskoci
(74) *Attorney, Agent, or Firm*—Darby & Darby P.C.

(57) ABSTRACT

A process for killing microorganisms and controlling biofouling in high chlorine demand waters comprises mixing two components, one of which is an oxidant and the other an ammonium salt, and adding the mixture immediately to the aqueous system to be treated.

14 Claims, No Drawings

OTHER PUBLICATIONS

J. Johnson et al. "Bromine and Bromamine Disinfection Chemistry" —Journal of the Sanitary Engineering Division, Oct. 1971 pp. 617-629.

C. Haas "Water Quality Treatment—Chapter 14 Disinfection" —pp. 877-894.

E. Mackenzie Report on a Series of Tests Performed to Ascertain the Efficiency of the Ammonia Chlorine Treatment of Water Applied by a Standardized Method.

G. Houghton "Experiments as to the Effect of pH and Organic Content in the Ammonia-Chlorine Treatment of Water" —Inst. of Water Engineers 4:5 434 (1950) pp. 434-444.

H. Phillips "White Water Utilization" —The Paper Mill, Jan. 28, 1933, 4 pgs.

W. Olszewski "The New Ammonia/Chlorine Gas Disinfecting Process" —Chemiker Zeitung No. 28 Apr. 9, 1927, 3 pgs.

W. Olszewski "The Monochloramine Process For Disinfecting Swimming Pool Water" Chemiker Zeitung No. 14, Feb. 18, 1928, 3 pgs.

"Chloramine at Denver Solves Aftergrowth Problem" —Engineering News-Record, vol. 79, No. 5 p. 210.

R. Hoather "The Bactericidal Effect of Ammonia-Chlorine Treatment, Residual Chloramine and Free Residual Chlorine" pp. 507-514.

Twenty-ninth Annual Report 1934—pp. 60-73.

S. Block, G. Dychidala "Chlorine and Chlorine Compounds" —Disinfection, Sterilization, and Preservation Third Edition pp. 157-173, 178-182.

* cited by examiner

PROCESS AND COMPOSITIONS FOR THE DISINFECTION OF WATERS

BACKGROUND OF THE INVENTION

Biological fouling of circulating water is a known and well documented problem. Several factors contribute to the problem and govern its extent: water temperature; water pH; organic and inorganic nutrients either from air drawn into the system or from materials naturally occurring in the water or continuously supplied during plant operation; aerobic/anaerobic conditions; the presence/absence of sunlight, etc.

Algae, fungi, bacteria, as well as other simple life forms are found in circulating water. The types of microorganisms and the extent of microbial growth depend on the water source and on the other factors.

Biological growth in circulating water can foul pipelines, accelerate corrosion, attack wood, decrease heat transfer, plug filters, cause imperfections in paper sheets; decompose sizing mixtures, and cause many other process interferences.

Oxidizing biocides including chlorine gas, hypochlorous acid, bromine and other oxidizing biocides are widely used in recirculating water.

"Chlorine demand" is defined as the quantity of chlorine that is reduced or otherwise transformed to inert forms of chlorine by substances in the water; and standard methods have been established for measuring it. In this specification and claims "chlorine demand" is as measured by procedures outlined in "Standard Methods for the examination of water and waste water,", 16th edition, Methods §409, pages 316-319. The methods are based on applying a specific dose of chlorine to the medium and measuring the residual chlorine left after a given contact time. Chlorine-consuming substances include ammonia and amino derivatives; sulfides, cyanides, oxidizable cations, pulp lignins, starch, sugars, oil, water treatment additives like scale and corrosion inhibitors.

Microbial growth in the water and in biofilms contribute to the chlorine demand of the water and to the chlorine demand of the system to be treated. Oxidizing biocides were found to be ineffective in waters containing a high chlorine demand, including heavy slimes. Non-oxidizing biocides are usually recommended for such waters.

Chlorination of water having a high content of ammonia or other amino-derivatives results in the formation of chloramines. Chloramines are described as poor biocides relative to hypochlorous or hypobromous acid. According to literature, chlormines are slow to react and may be more persistent in water systems (The NALCO water handbook. 1988, PCT/US 89/02730 21.6.1989, Great Lakes Chem. Corp. Wat. Sci. Tech. 20 No. 11/12, pp. 385-39, 1988, by M. D. Sobsey et al., National Academy of Science, 1980, Drinking Water and Health, Vol. 2, National Academy Press, Washington, D.C.).

Chloramination of drinking water occurs when chlorine reacts with small amounts of ammonia either present in or added to the water. Traditional chloramination occurs with the addition of free chlorine to the total amount of water for reaction with small amounts of ammonia present in the water, or added to the water in known amounts. Only one reference describes the use of pre-formed monochloramine for the post-disinfection of drinking water (J. Beck et al., Aqua I, 25-33, 1986). In this work, chloramines were formed by mixing ammonium sulfate and hypochlorite solution at a concentration of 1000 ppm; pH was adjusted to 7.5 before the point of dosage to avoid carbonate precipitation.

Chloramines were used to control aftergrowth and biofouling in the surface seawater reverse osmosis plants (Desalination 74, 51-67 (1989) and European Patent Application No. 9108872.4, 11.05.90, for Du Pont de Nemours and Company). This patent claims the use of chloramine to inhibit regrowth following dechlorination in liquid process streams containing chlorine degradable organic material, that when in degraded form provides energy and carbon source that is assimilable by microorganisms. The chloramine for the process was made in situ by adding $NH_3$ gas, $NH_4OH$, $NH_4Cl$ or $(NH_4)_2SO_4$. The sources of chlorine were $Cl_2$ gas, NaOCl, $Ca(OCl)_2$ and electrolytically generated chlorine.

Chloramines formed in situ during chlorination of cooling water containing ammonia, is considered to have no biocidal effect in the treatment of cooling towers, since chloramines are quickly stripped due to their high volatility [G. Holz Wart et al., Water Res. 18(1), 1421-1427 (1984)].

The disinfection of highly turbid waste water using chlorine had improved when ammonia was added to the waste water (in situ), when longer contact times were allowed [Atasi Khalil Z. et al.; Proc. Annu. Conf. Am. Water Works Assoc., 1988 (Pt. 2), pp. 1763-1770].

Ammonium bromide was not mentioned as a possible source for chloramines. The usual sources are ammonia, ammonium chloride and ammonium sulfate.

Its is a purpose of the invention to provide a process and compositions for killing microorganisms and inhibiting biofouling in waters, especially in cooling waters and aqueous systems having a high chlorine demand waters, and more especially in cooling waters and aqueous systems having a high chlorine demand.

It is another purpose of the invention to provide such a process and compositions that have a high biocidal effect and a high initial rate of kill in high chlorine demand waters.

It is further purpose of the invention to provide such a process and compositions the biocidal effect and the properties of which are constant and predetermined.

Other purposes and advantage of the invention will become apparent as the description proceeds.

SUMMARY OF THE INVENTION

The process according to the invention comprises mixing two components, one of which is an oxidant, preferably an active chlorine donor and still more preferably sodium hypochlorite, and the other, an ammonium salt, preferably chosen among halides, sulfates and nitrates, and adding the biocidal concentrate immediately to the aqueous system to be treated. The frequency, duration and concentration should be determined in each individual case so as to be sufficient to control biofouling.

Preferably, the two ingredients are mixed in a specific order, and specifically the oxidant is added to a solution of the ammonium salt. In a preferred form of the invention, the oxidant is NaOCl and is slowly added to a well-mixed solution of the ammonium salt diluted in the range of 0.01% to 2% equimolar to chlorine, preferably until a final concentration of chlorine in the mixture has reached 0.01-1% as chlorine. Either batch or continuous formation of the biocidal stock solution is effective.

The biocidal mixture was found to be more effective than other oxidizing biocides (such as chlorine or bromine) whenever the demand in the water system exceeds 1.8 ppm $Cl_2$ out of 2.0 ppm $Cl_2$ within 60 minutes. The percentage of ingredients are given as weight percent.

The mole ratio N/Cl is preferably 1:1. An excess of N may be used.

The temperature of the water to which the mixture is added, can be in the region of 10-60° C. The temperature of the solution of ammonium salt should be 10-30° C. when NaOCl is added. The pH is controlled by the concentration of the NaOCl solution; preferably the pH range should be 8.0-12.5. The active ingredient was effective at pH 7 and at pH 8. Some decrease in efficacy was noted at pH 9.

The frequency and duration of treatment and concentrations of active ingredient needed in order to maintain good control of biofouling should be determined in each individual case. However, good control was achieved at a level of 3 mg/l as chlorine (4.2 kg $NH_4Br$ for 1000 $m^3$).

The biocidal mixture is very effective for shock treatment of fouled systems, even in cases where the water demand is low, and enables the effective daily use of oxidizing biocides. A level of 9 mg/l (as chlorine) is sufficient to clean a fouled system.

In preferred forms of the invention, the mixture is formed and fed either batchwise or continuously by any suitable means, such as by a liquid metering pump or by gravity.

The invention comprises the solutions prepared as described above.

DETAILED DESCRIPTION OF PREFERRED EMBODIMENTS

The following are non-limitative examples of possible applications of the process:
Recirculating cool water
Brewery pasteurizer
Air washer
Evaporative cooling water
Scrubbers
Pond and lagoon water
Closed water-cooling systems
Food plant disinfection
Bleaching—pulp and paper
etc.

The process according to the invention is compatible with other water treatment chemicals, corrosion and scale inhibitors, etc.

EXAMPLE 1

Efficacy in Buffer at pH-7.5 against *Pseudomonas* sp.

Dosage: 1 ppm as $Cl_2$;
Chlorine demand: 0.1 ppm out of 1 ppm within 20 minutes
$NH_4Br+NaOCl$: stock concentration: 1000 ppm as $Cl_2$
Preparation of Stock Solution: $NH_4Br$ was Dissolved in do-Ionized Water (2761 ppm). NaOCl (2000 ppm as $Cl_2$) was quickly added dropwise to the ammonium bromide solution while stirring the mixture. The stock solution was used immediately.

TABLE I

| Biocide | Survivors (cfu/ml) | | after time (minutes) | |
| --- | --- | --- | --- | --- |
| | 1 | 5 | 10 | 20 |
| NaOCl | $4 \times 10^6$ | $1 \times 10^5$ | $4 \times 10^2$ | 0 |
| NaOCl + NaBr (1:1) | $5 \times 10^3$ | $4 \times 10^2$ | $4 \times 10$ | 0 |
| $NH_4Br$ + NaOCl (1:1) | $6 \times 10^6$ | $2 \times 10^6$ | $5 \times 10^3$ | 0 |
| Control | — | — | — | $9 \times 10^6$ |

Results in Table I indicate higher rates of kill for NaOBr and NaOCl as compared to $NH_4Br+NaOCl$ in water with low demand for chlorine.

EXAMPLE 2

Efficacy of Ammonium Bromide at Various pHs

Examined MO: *bacillus* mycoides
Dose: 2 ppm as $Cl_2$
$NH_4Br+NaOCl$: molar ratio 1:1; stock concentration: 0.5%;
$NH_4Br+NaOCl$ was either pre-mixed or added in situ to the buffer.
Demand: 1.8 ppm out of 2 ppm of $Cl_2$ within 60 minutes.

TABLE II

| | Survivors: cfu/ml | | | | | | | | |
| --- | --- | --- | --- | --- | --- | --- | --- | --- | --- |
| | pH-7.0 | | | pH-8.0 | | | pH-9.0 | | |
| Treatment | 60 m | 180 m | 24 h | 60 m | 180 m | 24 h | 60 m | 180 m | 24 h |
| $NH_4Br$ + NaOCl premix | $7 \times 10^4$ | $2 \times 10^4$ | $2 \times 10^2$ | $2 \times 10^5$ | $9 \times 10^4$ | $2 \times 10^2$ | $1 \times 10^5$ | $9 \times 10^4$ | $1 \times 10^4$ |
| $NH_4Br$ + NaOCl in situ | $2 \times 10^5$ | $6 \times 10^4$ | $2 \times 10^4$ | $1 \times 10^5$ | $7 \times 10^4$ | $1 \times 10^4$ | $2 \times 10^5$ | $1 \times 10^5$ | $1 \times 10^5$ |
| NaOCl | $1 \times 10^5$ | $1 \times 10^5$ | $1 \times 10^5$ | $3 \times 10^5$ | $1 \times 10^5$ | $1 \times 10^5$ | $1 \times 10^5$ | $1 \times 10^5$ | $1 \times 10^5$ |
| NaOCl + NaBr 1:1 | $2 \times 10^5$ | $1 \times 10^5$ | $1 \times 10^5$ | $3 \times 10^5$ | $2 \times 10^5$ | $2 \times 10^5$ | $2 \times 10^5$ | $1 \times 10^5$ | $1 \times 10^5$ |
| non-treated | — | $3 \times 10^6$ | $5 \times 10^5$ | $3 \times 10^6$ | — | $1 \times 10^5$ | $5 \times 10^5$ | — | $4 \times 10^5$ |

Table II shows that pre-mixed ($NH_4Br+NaOCl$) a higher rate of kill as compared to either NaOCl or NaOBr, as the demand for chlorine increases. Efficacy was slightly impaired at pH from 8.0 to 9.0.

EXAMPLE 3

Efficacy of $NH_4Cl+NaOCl$ in Water Taken from a Citrus Juice Evaporator: Comparison to Non-Oxidizing Biocides Water demand: higher than 30 ppm of $Cl_2$ (out of 30 ppm $Cl_2$) within 60 minutes.
Concentration of stock solution ($NH_4Cl+NaOCl$): 1000 ppm.
Algicol II is a quaternary ammonium salt.

TABLE III

| Biocide | Survivors (cfu/ml) dose mg/l | 1 | 24 | after time (hours) 7 days |
|---|---|---|---|---|
| Kathon | 30 | $2 \times 10^6$ | $7 \times 10^2$ | $7 \times 10^2$ |
| MBT | 30 | $1 \times 10^6$ | $1 \times 10^3$ | $8 \times 10^2$ |
| Algicol II | 100 | $5 \times 10^6$ | $4 \times 10^6$ | $9 \times 10^6$ |
| $NH_4Cl + NaOCl$ | 30 | 0 | 0 | 0 |
| Control | — | $6 \times 10^6$ | $3 \times 10^7$ | $1 \times 10^7$ |

Results in Table III indicate that a mixture of $NH_4Cl+NAOCl$ was more effective than 3 non-oxidizing biocides in water with high demand for chlorine.

EXAMPLE 4

Efficacy of Oxidizing and Non-Oxidizing Biocides is a Starch Sizing Mixture (Paper Industry)

Efficacy was measured at 60° C.
$NH_4Br+NaOCl$: stock concentration 0.1%.
Dosage: 30 ppm active ingredient.
Incubation temperature 60° C.

TABLE IV

| Biocide | Surviving MOs (cfu/ml) 4 | 28 | after time (hours) 48 | 72 |
|---|---|---|---|---|
| MBT | $9 \times 10^4$ | $4 \times 10^4$ | $2 \times 10^4$ | $2 \times 10^4$ |
| NaOCl + NaBr | $4 \times 10^3$ | $6 \times 10^5$ | $3 \times 10^5$ | $3 \times 10^6$ |
| NaOCl | $4 \times 10^3$ | $2 \times 10^6$ | $3 \times 10^6$ | $3 \times 10^6$ |
| NaOCl + $NH_4Br$ | $2 \times 10$ | 3 | 0 | 0 |
| MIT | $2 \times 10^4$ | $2 \times 10^3$ | $2 \times 10^3$ | $1 \times 10^3$ |
| DBNPA | $3 \times 10^4$ | $2 \times 10^5$ | $2 \times 10^5$ | $1 \times 10^5$ |
| Control | $1 \times 10^5$ | $3 \times 10^5$ | $8 \times 10^5$ | $7 \times 10^5$ |

Results in Table IV prove that a mixture of $NH_4Br+NaOCl$ is more effective than other oxidizing and non-oxidizing biocides in a high demand medium.

EXAMPLE 5

Kinetics of Kill of Various Mixtures of Ammonium Salts Mixed with NaOCl in Water from a Citrus Juice Evaporator Dosage: 30 ppm as $Cl_2$
Demand: Higher than 30 ppm out of 30 ppm of $Cl_2$ during 10 minutes.
Stock concentration of $NH_4X+NaOCL$: 0.1% as $Cl_2$

TABLE V

| Biocide | residue as $Cl_2$ free (total) after time (minutes) | | | Surviving MOs after time (minutes); total aerobic (total anaerobic) cfu/ml | | |
|---|---|---|---|---|---|---|
| | 10 | 20 | 60 | 10 | 20 | 60 |
| $NH_4Cl + NaOCl$ | 5 (10) | 1 (2) | 0 (0) | $5 \times 10^2 (4 \times 10^2)$ | $3 \times 10^2 (2 \times 10^2)$ | $1 \times 10^2 (3)$ |
| $NH_4Br + NaOCl$ | 0 (0) | 0 (0) | 0 (0) | $4 \times 10^2 (4 \times 10^2)$ | $5 \times 10^2 (4 \times 10^2)$ | $5 \times 10^2 (2 \times 10^2)$ |
| $NH_4NO_3 + NaOCl$ | 6 (9) | — | 0 (0) | $4 \times 10^2 (2 \times 10)$ | $4 \times 10^2 (7)$ | $8 \times 10 (2)$ |
| NaOCl | 0 (0) | 0 (0) | 0 (0) | $2 \times 10^5 (8 \times 10^4)$ | $2 \times 10^7 (3 \times 10^6)$ | $1 \times 10^7 (3 \times 10)$ |
| NaOCl + NaBr | 0 (0) | 0 (0) | 0 (0) | $2 \times 10^7 (4 \times 10^6)$ | $1 \times 10^7 (3 \times 10^8)$ | $2 \times 10^7 (2 \times 10^6)$ |
| CONTROL | — | — | — | — | — | $2 \times 10^7 (6 \times 10^6)$ |

Results in Table V show that mixtures of ammonium salts and NaOCl are effective in controlling aerobic and anaerobic microorganisms in water with high demand for chlorine. Control was achieved within 10 minutes. Under these conditions both NaOCl and NaOBr are impaired by the media. The mixture of $NH_4Br+NaOCl$ did not leave a measurable residue after 10 minutes, yet it was very effective in reducing viable count within 10 minutes.

EXAMPLE 6

Efficacy of Oxidizing Biocides in Water Taken from Paper Mill (Thick Stock of Pulp Slurry)

Dose: 15 mg/l as $Cl_2$
Microorganisms were incubated at 37° C. (total aerobic viable counts). Concentration of stock solution: 0.1% as $Cl_2$.

TABLE VI

| Biocide | Viable 30 | counts cfu/ml 70 | after time (minutes) 25 hours |
|---|---|---|---|
| DBNPA | $2 \times 10^3$ | $6 \times 10$ | $8 \times 10$ |
| NaOCl | $6 \times 10^3$ | $2 \times 10^3$ | $1 \times 10^5$ |
| NaOCl + NaBr | $1 \times 10^4$ | $5 \times 10^3$ | $2 \times 10^6$ |
| $NH_4Br + NaOCl$ | 1 | 0 | 0 |
| CONTROL | $7 \times 10^6$ | — | $1 \times 10^7$ |

Results in Table VI prove higher efficacy for $NH_4Br+NaOCl$ as compared to other oxidizing biocides in this heavily loaded water.

EXAMPLE 7

Efficacy of a Series of Biocides in Domestic Waste Containing a High Concentration of Amines Contact time: 10 minutes
Dose: 60 ppm as $Cl_2$
Incubation temperature: 27° C.
Stock concentration: 0.2%
N as $NH_3$: 50 mg/l; pH: 6.10.

TABLE VII

| Biocide | Residue free (total) as $Cl_2$ after 10 minutes | Surviving MOs (cfu/ml) after 10 minutes | | |
| --- | --- | --- | --- | --- |
| | | aerob. | anaer. | fungi |
| NaOCl | 0.2 (1.5) | $9 \times 10^2$ | $3 \times 10^3$ | $2 \times 10$ |
| $NH_4Cl$ + NaOCl | 3.0 (9.0) | $2 \times 10^2$ | $4 \times 10^2$ | 0 |
| DBNPA | 0 (0) | $2 \times 10^6$ | $5 \times 10^5$ | 0 |
| Control | — | $5 \times 10^7$ | $1 \times 10^6$ | $2 \times 10$ |

Results in Table VII prove that in the presence of a high $NH_3$ concentration, NaOCl was less effective than pre-mixed $NH_4Cl$+NaOCl in controlling microbial growth (in water with high demand for $Cl_2$): good control was measured after 10 minutes.

EXAMPLE 8

Efficacy of Oxidizing Biocides in Domestic Waste

Non-treated domestic waste roughly filtered; contact time: 10 minutes.
Stock concentration: 0.5% as $Cl_2$.
Dose: 20 ppm as $Cl_2$

TABLE VIII

| treatment | residue as $Cl_2$ ppm free (total) | Fecal *coli* cfu/ml | total count cfu/ml |
| --- | --- | --- | --- |
| NaOCl | 0 (0) | $5 \times 10^5$ | $6 \times 10^6$ |
| NaOCl + NaBr (1:1) | 0 (0) | $3 \times 10^5$ | $7 \times 10^6$ |
| NaOCl + $(NH_4)_2SO_4$ (1:1) | 0.05 (0.7) | $3 \times 10^3$ | $3 \times 10^4$ |
| non-disinfected | | $5 \times 10^5$ | $1 \times 10^7$ |

Results in Table VIII prove that pre-mixing $(NH_4)_2SO_4$ with NaOCl resulted in lower viable counts of both fecal coli and total count.

In waste water with high organic load, this disinfection method was superior to disinfecting with either NaOCl or NaOBr.

EXAMPLE 9

Efficacy of Biocides in the Presence of Anti-Scale and Corrosion Inhibiting Treatment (CWC)

Stock concentration: 0.5% as $Cl_2$
Efficacy against *pseudomonas* sp.
CWC: 100 mg/l
pH: 9.0
Contact time: 5 hours

TABLE IX

| treatment | dose mg/l | Survivors in buffer | Survivors in CWC (100 mg/l) |
| --- | --- | --- | --- |
| DBNPA | 4 | 0 | $4 \times 10^6$ |
| BCDMH | 4 | 0 | $3 \times 10^5$ |
| $NH_4Br$ + NaOCl | 1 | 0 | $1 \times 10^3$ |
| | 5 | 0 | $2 \times 10$ |

Results in Table IX prove that in the presence of scale and corrosion inhibitors, efficacy of various biocides was impaired to such an extent that much higher dosages of biocides had to be fed in order to maintain good control. The mixture of $NH_4Br$+NaOCl was less impaired by CWC and established good microbial and algal control even in the presence of CWC.

EXAMPLE 10

Pre-Mixing Versus In Situ Addition of Ammonium Salts and NaOCl

Water from a corn-processing plant; high deed for $Cl_2$.
Dose: 12 ppm
$NH_4Cl$+NaOCl: stock concentration: 1%
$NH_4Br$+NaOCl: stock concentration: 0.5%
Stock solutions were formed at pH 14.0; 7.0, 4.0 and in water.
For in situ addition: both $NH_4X$ and NaOCl were dissolved at the appropriate pH.

TABLE X

| Treatment | Survivors cfu/ml (total count after time in minutes) buffer | | | | | | | |
| --- | --- | --- | --- | --- | --- | --- | --- | --- |
| | pH-14.0 | | pH-7.0 | | pH-4.0 | | $H_2O$ | |
| | 60 | 180 | 60 | 180 | 60 | 180 | 60 | 180 |
| $NH_4Br$ + NaOCl | $1 \times 10^6$ | $8 \times 10^5$ | $2 \times 10^5$ | $1 \times 10^6$ | $1 \times 10^6$ | $1 \times 10^6$ | $6 \times 10^4$ | $1 \times 10^4$ |
| $NH_4Cl$ + NaOCl | $1 \times 10^5$ | $1 \times 10^5$ | $6 \times 10^4$ | $6 \times 10^3$ | $7 \times 10^5$ | $1 \times 10^6$ | $5 \times 10^4$ | $7 \times 10^3$ |
| $NH_4Br$ + NaOCl in situ | $1 \times 10^6$ | $2 \times 10^6$ | — | — | $2 \times 10^6$ | $2 \times 10^6$ | $5 \times 10^6$ | — |
| $NH_4Cl$ + NaOCl in situ | $8 \times 10^5$ | $2 \times 10^5$ | — | — | $1 \times 10^6$ | $1 \times 10^6$ | $2 \times 10^6$ | $2 \times 10^6$ |
| NaOCl | — | — | — | — | — | — | $2 \times 10^6$ | $2 \times 10^6$ |
| NaOCl + NaBr | — | — | — | — | — | — | $3 \times 10^6$ | $3 \times 10^6$ |
| Control | | | | | | | $4 \times 10^6$ | — |

Results in Table X prove that the efficacy exhibited by mixture of $NH_4X+NaOCl$ depend on the pH and on the mode of formation of the stock mixture. In situ addition of the two ingredients to water resulted in lower efficacy at any of the examined pH's.

Stock mixture of $NH_4Br+NaOCl$ was more effective when prepared in water than when prepared in buffer at pH 7.0. When the stock solution was prepared at a high or at a low pH, it was less effective.

EXAMPLE 11

Dependence of Efficacy of Mixtures of $NH_4Br+NaOCl$ on the Concentrations of Stock Solution Work was carried out in industrial waste water.
Stock concentrates were prepared in buffer at pH 7.00.
Biocidal dose: 4 ppm as $Cl_2$.

TABLE XI

| treatment | Survivors cfu/ml total count after time (minutes) | | |
|---|---|---|---|
| $NH_4Br + NaOCl$ | 10 | 60 | 180 |
| 2% | $6 \times 10^4$ | $1 \times 10^4$ | $2 \times 10^3$ |
| 1% | $2 \times 10^5$ | $3 \times 10^4$ | $3 \times 10^4$ |
| 0.5% | $7 \times 10^4$ | $2 \times 10^4$ | $4 \times 10^3$ |
| 0.01% | $2 \times 10^6$ | — | $2 \times 10^6$ |
| in situ | $5 \times 10^5$ | $3 \times 10^5$ | $5 \times 10^5$ |
| NaOCl | $9 \times 10^5$ | — | $7 \times 10^5$ |
| Control | $1 \times 10^6$ | — | — |

Results in Table XI prove that the efficacy exhibited by the mixtures correlated with the concentration of stock solutions. The highest efficacy was measured with a stock concentration equal to at 0.5% as $Cl_2$. Similar trends were obtained when the stock solutions were prepared in water rather than in buffer (Bee Table X) (The high efficacy measured in buffer at a level of 2% as $Cl_2$ results from the higher pH of this mixture.)

FIELD EXPERIMENTS

Example I

Cooling Tower 1

Cooling tower; contained volume 1000 $m^3$
Circulation rate 500 $m^3/h$
Scale and corrosion inhibitor: CWC: 100 mg/l The tower was controlled on low level (0.6-1.2 kg/day) of BCDMH feed. Use of BCDMH was effective as long as make-ups were softened in ion-exchangers.

When CWC (100 mg/l of phosphonate) replaced the use of ion-exchangers, much higher dosages of BCDMH (4-5 kg/day) did not suffice to prevent biofouling and growth of algae.

The system was shock-fed with $NH_4Br+NaOCl$. Overall dosage: 75 liters NaOCl (10%) 12.6 kg $NH_4Br$. The mixture was fed during 1.5 hours. This shock treatment cleaned the systems.

A slug dose of 25 liters NaOCl (10% as $Cl_2$) (+4.2 kg $NH_4Br$) was then fed to the cooling tower once in two to three days. The cooling tower remained clean, with no apparent growth of biofilm or algae. A measurable residue of 0.6-0.4 ppm (as total chlorine) was measured in the water 24 and 48 hours after feeding the mixture.

Example II

Cooling tower 2

Corn processing plant.
Contained volume: 20 $m^3$
Circulation rate: 300 $m^3/h$
pH: 7.5-8.0
Water temperature: 36° C.-57° C.

This tower was treated with BCDMH (1.50-2.26 kg/day) daily. Due to a very high organic load in the water, growth of biofilm was very fast. Treatment with BCDMH was effective in controlling the daily grown films, but was not effective against heavy slimes which covered the cooling tower.

A daily feed of 3 liters NaOCl (7% as $Cl_2$), mixed with 0.35 kg $NH_4Br$ controlled the daily newly formed biofilm as well as the slime and algae growth covering the cooling tower, and left a clean cooling system after three weeks of daily treatment avoiding the need for shock treatment.

Example III

Starch Sizing Mixture

Paper mill, starch sizing
Contained volume: 20 $m^3$
Flow rate: 8.33 $m^3/h$. (6% starch in $H_2O$),
pH about 8.0
Temperature: 50° C.-70° C.

Sizing mixture is recirculated in a size press through a filter (80 microns). Circulation rate: 6 $m^3/h$. The sizing mixture had been previously treated with NaOCl (10% as $Cl_2$), which was fed every 8 hours (30 liters per portion). With this treatment, filters had to be washed once every two hours.

Use of NaOCl was replaced by the use of a mixture of $NH_4Br+NaOCl$ (stock concentration 0.5% as $Cl_2$).

Feeding of NaOCl (13 liters of 10% as $Cl_2$) and $NH_4Br$ (2.5 kg) three times a day (every eight hours) kept the filters in the size press dean; the treatment with $NH_4Br+NaOCl$ was compatible with a blue dye added to the sizing mixture, and did not bleach the blue starch, unlike NaOCl.

A number of embodiments of the invention have been described for purposes of illustration, but it will be understood that they are not limitative and that the invention can be carried out by persons skilled in the art with many modifications, variations and adaptations, without departing from its spirit and from the scope of the appended claims.

The invention claimed is:

1. A process for killing microorganisms and controlling biofouling in high chlorine demand water, which comprises mixing a solution of sodium hypochlorite and a solution of at least one ammonium salt in a molar ratio calculated as N/Cl of at least 1:1, wherein the solutions are prepared in water without a buffer, to form a biocidal mixture, the concentration of said mixture being 0.01% to 2.0% as $Cl_2$ and adding said mixture to said high chlorine demand water immediately following said mixing, said ammonium salt being selected from ammonium chloride and ammonium bromide.

2. A process according to claim 1, wherein said high chlorine demand water is water in the pulp and paper industry.

3. A process according to claim 1, wherein said ammonium salt is ammonium bromide.

4. A process according to claim 1, wherein said sodium hypochlorite is added to a solution of said ammonium salt.

5. A process according to claim 4, wherein said sodium hypochlorite is added to a well-mixed solution of said ammonium salt in the range of 0.1% to 1%, until the full concentration of chlorine in said mixture has reached 0.1-1%.

6. A process according to claim 1, wherein said high chlorine demand water has a chlorine demand of at least 1.8 ppm out of 2.0 ppm $Cl_2$ after 60 minutes.

7. A process according to claim 1, wherein said mixture is added to said high chlorine demand water at a daily level of at least 2 mg/l as $Cl_2$.

8. A process according to claim 1, wherein the temperature of said mixture is 10-30 degrees Celsius.

9. A process according to claim 1, wherein said mixture is fed continuously to said high chlorine demand water.

10. A process according to claim 1, wherein said mixture has a pH of 8.0 to 12.5.

11. A process according to claim 1, wherein said high chlorine demand water is recirculating water.

12. A process according to claim 1, wherein said ammonium salt is ammonium chloride.

13. A process according to claim 1, wherein the concentration of said sodium hypochlorite/ammonium salt mixture is from 0.1% to 0.5% $Cl_2$.

14. A process according to claim 1, wherein the temperature of said high chlorine demand water to which said mixture is added is 10-60 degrees Celsius.

* * * * *